United States Patent
Nojima et al.

(10) Patent No.: US 7,846,972 B2
(45) Date of Patent: Dec. 7, 2010

(54) MULTIMERIC OLEAMIDE DERIVATIVE HAVING CONNEXIN-26 INHIBITING POTENCY AND USE THEREOF IN CANCER THERAPY, ETC

(75) Inventors: Hiroshi Nojima, Osaka (JP); Yasuyuki Kita, Osaka (JP)

(73) Assignees: The New Industrial Research Organization, Kobe (JP); Osaka University, Osaka (JP)

( * ) Notice: Subject to any disclaimer, the term of this patent is extended or adjusted under 35 U.S.C. 154(b) by 686 days.

(21) Appl. No.: 11/718,361
(22) PCT Filed: Nov. 1, 2005
(86) PCT No.: PCT/JP2005/020089
§ 371 (c)(1), (2), (4) Date: May 1, 2007
(87) PCT Pub. No.: WO2006/049157
PCT Pub. Date: May 11, 2006

(65) Prior Publication Data
US 2008/0089924 A1 Apr. 17, 2008

(30) Foreign Application Priority Data
Nov. 2, 2004 (JP) .................. 2004-319630

(51) Int. Cl.
A01N 37/18 (2006.01)
A61K 31/195 (2006.01)
A61K 47/00 (2006.01)
C07C 233/00 (2006.01)

(52) U.S. Cl. .................. 514/613; 514/561; 424/439; 554/35

(58) Field of Classification Search .................. 514/561, 514/613
See application file for complete search history.

(56) References Cited
U.S. PATENT DOCUMENTS
3,872,120 A * 3/1975 Mod et al. .................. 544/335
3,875,159 A 4/1975 Mod FOREIGN PATENT DOCUMENTS
JP 2001-017184 A 1/2001
(Continued)

OTHER PUBLICATIONS
Cancer, Encyclopaedia Britannica, 2007, Encyclopaedia Britannica Online 24, pp. 1-46.*
(Continued)

Primary Examiner—Daniel M Sullivan
Assistant Examiner—Yate' K Cutliff
(74) Attorney, Agent, or Firm—Roylance, Abrams, Berdo & Goodman, LLP

(57) ABSTRACT

The present invention relates to multimeric oleamide derivatives having connexin 26 inhibitory activities and embraces the dimer oleamide derivatives represented by the following formula (1) or a pharmacologically acceptable salt thereof:

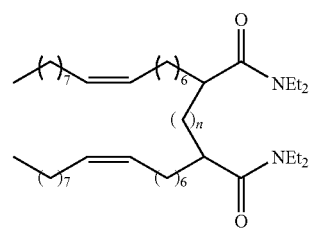

where n denotes an integer of 3, 5, or 8. The novel oleamide derivatives of the present invention can be used not only as research reagents, but also in a wide industrial field because they exhibit useful bioactivities such as cancer metastasis/growth inhibition. Thus they have various applications, such as in medicines, supplements, and functional foods, in addition to cancer-preventive and cancer-therapeutic drugs.

3 Claims, 5 Drawing Sheets

FOREIGN PATENT DOCUMENTS

WO           99/26584 A2     6/1999
WO        2004/060398 A1     7/2004

OTHER PUBLICATIONS

Lee, et al., Transcriptional downregulatin of Gap-junction Proteins Blocks Junctional Communication in Human mammary Tumor Cell Lines, 1992, The Journal of Cell Biology, vol. 118, No. 5, pp. 1213-1221.*

Duflot-Dancer et al., Dominant-negative abrogatio of connexin-mediated cell growth control by mutant connexin genes, 1997, Oncogene, vol. 15, pp. 2151-2158.*

Ito A. et al.: A role for heterologous gap junctions between melanome and ethothelial cels in metastasis, J. Clin. Invest. 105:1189-1197, 2000.

Boger D. L. et al.: Chemical requirement for inhibition of gap junction communication by the biologically active lipid oleaminde, Proc. Nat. Acad. Sci. USA. 95:4810-4815. 1998.

* cited by examiner (a)

Control (b)

MI-22

MULTIMERIC OLEAMIDE DERIVATIVE HAVING CONNEXIN-26 INHIBITING POTENCY AND USE THEREOF IN CANCER THERAPY, ETC

This application is the U.S. National Phase under 35 U.S.C. §371 of International Application PCT patent application Ser. No. PCT/JP2005/020089, filed on Nov. 1, 2005, which claims priority to Japanese Patent Application No. 2004-319630, filed on Nov. 2, 2004. The International Application was published under PCT Article 21(2) in a language other than English. The contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to multimeric oleamide derivatives with connexin 26 inhibitory activities, and their use. These novel oleamide derivatives can be used not only as research reagents, but also in a wide industrial field because they exhibit useful bioactivities such as cancer metastasis/growth inhibition. Thus they have various applications, such as in medicines, supplements, and functional foods, in addition to cancer-preventive and cancer-therapeutic drugs.

BACKGROUND ART

Connexin is a generic term for a family of membrane-associated proteins that form gap junctions. More than 12 subtypes of connexin have been found that are different in molecular weight from one another. Connexin with a molecular weight of 26 kDa is referred to as connexin 26, and with a molecular weight of 43 kDa it is referred to as connexin 43.

A hexamer of connexin is called a connexon. It forms a channel-like structure to penetrate cell membranes. A gap junction is formed of connexons connected to one another between adjacent cells. This connection results in the formation of a channel, through which ions and low molecular weight proteins are transferred from cell to cell. This mechanism is considered necessary, for example, to sustain the homeostatic growth of epithelial cells.

Through basic researches to find a cancer metastasis mechanism at a genetic level, the inventors of the present invention have found that connexin 26 is closely related to cancer metastasis, more specifically, the inhibition of a connexin 26 function inhibits cancer metastasis (Patent Document 1 and Nonpatent Document 1, described below).

The examples of known substances that inhibit gap junctions include oleamide, an amide derivative of oleic acid, and a derivative thereof (Nonpatent Document 2, described below). The present inventors identified the derivatives selected from oleamide derivatives that specifically inhibit connexin 26 and exhibit high cancer metastasis inhibitory activities. One was then named "MI-18" (Patent Document 2, described below).

Patent Documents 3 and 4, explained below, describe examples in which dimer oleamide derivatives are used as raw materials of imidazolidine. Also described is that the imidazolidine, which is a product, has an activity inhibiting the growth of, for example, bacteria and yeast in vitro.

[Patent Document 1] Japanese Laid-Open Patent Publication No. 2001-17184
[Patent Document 2] International Publication WO 2004/060398
[Patent Document 3] U.S. Pat. No. 3,872,120
[Patent Document 4] U.S. Pat. No. 3,875,159
[Nonpatent Document 1] Ito, A. et al.: J. Clin. Invest., 105:1189-1197, 2000
[Nonpatent Document 2] Boger, D. L. et al.: Proc. Nat. Acad. Sci. USA., 95:4810-4815. 1998)

DISCLOSURE OF INVENTION

In current cancer therapy, cancer cells are treated directly, for example, by the administration of an anticancer agent, extirpation of cancer cells and cancer tissues, and radiation therapy. However, because cancer cells metastasize quite quickly, they often metastasize to other tissues during cancer therapy. As a result, the therapy is prolonged or cancer cells metastasize widely, which may result in death.

Therefore in order to improve the effects of cancer therapy, it is important to inhibit cancer metastasis in addition to direct cancer therapy through the administration of anticancer agents and the extirpation of cancer tissues, for example. However, the research and development of cancer metastasis inhibitors has been proceeding with difficulties, and no clinically established cancer metastasis inhibitors have been developed.

As described above, the present inventors have identified oleamide derivatives such as MI-18 that specifically inhibit connexin 26 and exhibit high cancer metastasis inhibitory activities. In order to use them industrially for pharmaceutical development, there are demands to explore better substances and to identify oleamide derivatives that exhibit high connexin 26 inhibitory activities and that are also excellent, for example, in easy handling, stability, and nontoxicity. It is possible that the oleamide derivatives thus obtained are also very useful as cancer metastasis inhibitors.

The present invention has been made with the aforementioned situation in mind and is intended to develop novel oleamide derivatives having connexin 26 inhibitory activities. The present invention is also intended to provide medicines, supplements, functional foods, and research reagents, each of which is obtained by using the novel oleamide derivatives obtained according to the present invention.

The present inventors synthesized various multimeric oleamide derivatives with structural stability and then explored substances that exhibited connexin 26 inhibitory activities among them by dye transfer assay. As a result, they found a plurality of novel oleamide derivatives that specifically inhibit connexin 26. Among them, MI-22, described later, which exhibited a high connexin 26 inhibitory activity, considerably inhibited spontaneous metastasis of cancer with hardly any cytotoxicity and thus was a biologically safe substance, was an oily matter easy to handle, and also was proved to have cancer growth inhibitory potential (antitumor effects). Based on these findings, it was found that the novel oleamide derivatives thus obtained could be used for pharmaceutical development, for example, as an anticancer spontaneous metastasis agent and as an anticancer growth agent. Further, they are also useful as supplements, functional foods, research reagents, and in other ways. Thus the present invention was completed.

That is, the present invention is a medically and industrially useful invention and embraces the following inventions (A) to (L).

(A) A dimer oleamide derivative represented by the following formula (1) or a pharmacologically acceptable salt thereof:

[Formula 1]

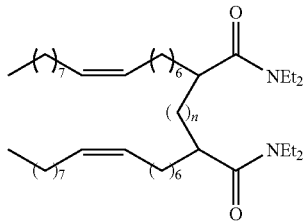

(1)

where n denotes an integer of 3, 5, or 8, carbon and hydrogen are omitted according to conventional notation, the numerals each denote the number of repeated hydrocarbons, and "$Et_2$" denotes a diethyl group. The same applies to the other formulas.

In formula (1) above, the one obtained when n=3 is hereinafter referred to as "MI-22". Similarly, in formula (1) above, those obtained when n=5 and n=8 are hereinafter referred to as "MI-39" and "MI-40", respectively.

(B) A dimer oleamide derivative represented by the following formula (2) or a pharmacologically acceptable salt thereof:

[Formula 2]

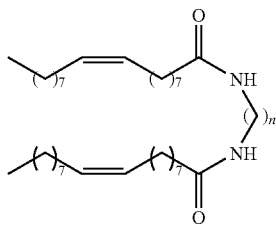

(2)

where n denotes an integer of 3 or 5.

In formula (2) above, those obtained when n=3 and n 5 are hereinafter referred to as "MI-45" and "MI-46", respectively.

(C) A dimer oleamide derivative represented by the following formula (3) or a pharmacologically acceptable salt thereof:

[Formula 3]

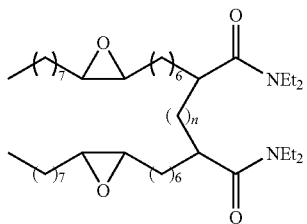

(3)

where n donates an integer of 5 or 8.

In formula (3) above, those obtained when n=5 and n=8 are hereinafter referred to as "MI-41" and "MI-42", respectively.

(D) A dimer oleamide derivative represented by the following formula (4) or a pharmacologically acceptable salt thereof:

[Formula 4]

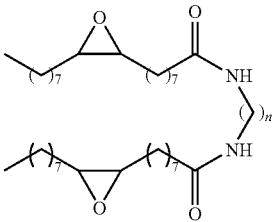

(4)

where n denotes an integer of 3 or 5.

In formula (4) above, those obtained when n 3 and n 5 are hereinafter referred to as "MI-47" and "MI-48", respectively.

(E) A trimer oleamide derivative represented by the following formula (5) or a pharmacologically acceptable salt thereof:

[Formula 5]

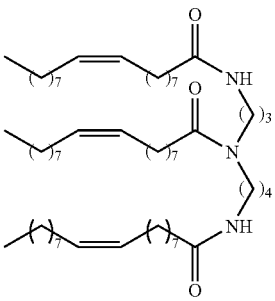

(5)

The oleamide derivative represented by formula (5) above is hereinafter referred to as "MI-50".

(F) A tetramer oleamide derivative represented by the following formula (6) or a pharmacologically acceptable salt thereof:

[Formula 6]

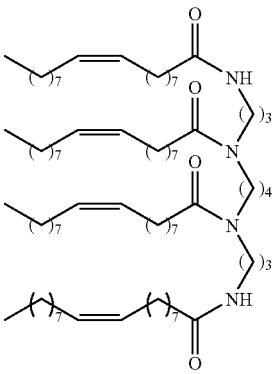

(6)

The oleamide derivative represented by formula (6) above is hereinafter referred to as "MI-52".

(G) A trimer oleamide derivative represented by the following formula (7) or a pharmacologically acceptable salt thereof:

[Formula 7]

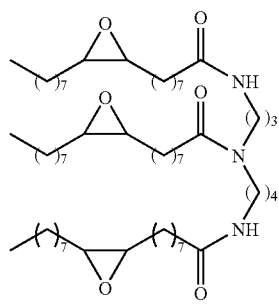

(7)

The oleamide derivative represented by formula (7) above is hereinafter referred to as "MI-51".

(H) A tetramer oleamide derivative represented by the following formula (8) or a pharmacologically acceptable salt thereof:

[Formula 8]

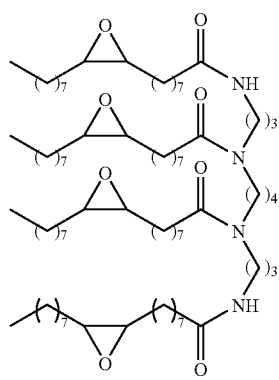

(8)

The oleamide derivative represented by formula (8) above is hereinafter referred to as "MI-53".

(I) A cancer metastasis inhibitor containing, as an active component thereof, a multimeric oleamide derivative represented by any one of formulas (1) to (8) above or a pharmacologically acceptable salt thereof.

(J) A cancer growth inhibitor containing, as an active component thereof, a multimeric oleamide derivative represented by any one of formulas (1) to (8) above or a pharmacologically acceptable salt thereof.

(K) A food composition containing a multimeric oleamide derivative represented by any one of formulas (1) to (8) above or a pharmacologically acceptable salt thereof.

(L) A connexin 26 inhibitor containing a multimeric oleamide derivative represented by any one of formulas (1) to (8) above or a pharmacologically acceptable salt thereof.

The term "multimeric" used in this specification denotes that a plurality of carbon chains of fatty acid are contained. For instance, the term "dimer" denotes that two carbon chains of fatty acid are contained. Similarly, the terms "trimer" and "tetramer" denote that three and four carbon chains of fatty acid are contained, respectively.

Oleamide derivatives of the present invention, i.e., multimeric oleamide derivatives represented by formulas (1) to (8) above, inhibit the function of connexin 26 to suppress/inhibit the spontaneous metastasis of cancer and therefore are useful as cancer-preventive drugs and cancer-therapeutic drugs. Furthermore, they can be used as supplements and functional foods besides their use as medicines. They also can be used for research reagents (biochemical reagents), for example, as connexin 26 inhibitors.

Paragraph 1. A dimer oleamide derivative represented by the following formula (1) or a pharmacologically acceptable salt thereof:

[Formula 1]

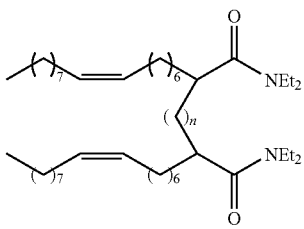

(1)

where n denotes an integer of 3, 5, or 8.

Paragraph 2. A dimer oleamide derivative represented by the following formula (2) or a pharmacologically acceptable salt thereof:

[Formula 2]

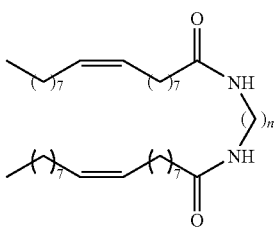

(2)

where n denotes an integer of 3 or 5.

Paragraph 3. A dimer oleamide derivative represented by the following formula (3) or a pharmacologically acceptable salt thereof:

[Formula 3]

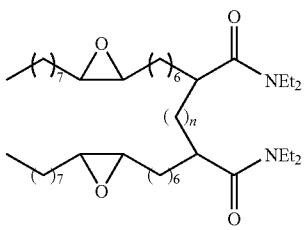

(3)

where n denotes an integer of 5 or 8.

Paragraph 4. A dimer oleamide derivative represented by the following formula (4) or a pharmacologically acceptable salt thereof:

[Formula 4] (4)

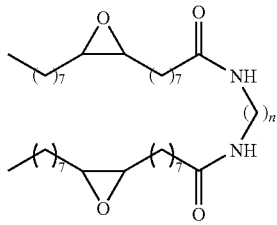

where n denotes an integer of 3 or 5.

Paragraph 5. A trimer oleamide derivative represented by the following formula (5) or a pharmacologically acceptable salt thereof:

[Formula 5] (5)

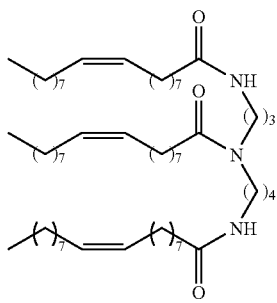

Paragraph 6. A tetramer oleamide derivative represented by the following formula (6) or a pharmacologically acceptable salt thereof:

[Formula 6] (6)

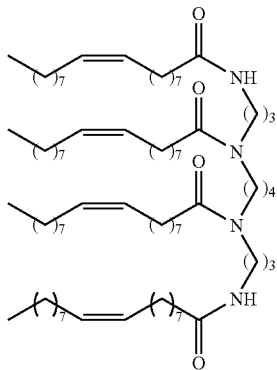

Paragraph 7. A trimer oleamide derivative represented by the following formula (7) or a pharmacologically acceptable salt thereof:

[Formula 7] (7)

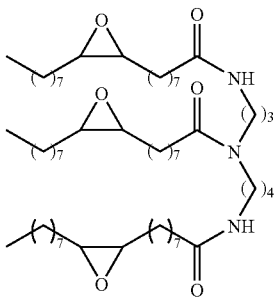

Paragraph 8. A tetramer oleamide derivative represented by the following formula (8) or a pharmacologically acceptable salt thereof:

[Formula 8] (8)

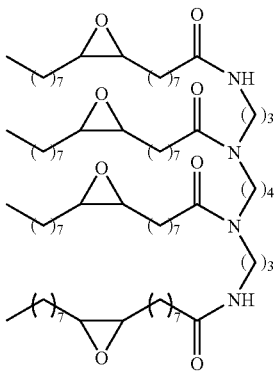

Paragraph 9. A cancer metastasis inhibitor comprising, as an active component thereof, a multimeric oleamide derivative represented by any one of formulas in Paragraphs (1) to (8) above or a pharmacologically acceptable salt thereof.

Paragraph 10. A cancer growth inhibitor comprising, as an active component thereof, a multimeric oleamide derivative represented by any one of formulas in Paragraphs (1) to (8) above or a pharmacologically acceptable salt thereof.

Paragraph 11. A food composition comprising a multimeric oleamide derivative represented by any one of formulas in Paragraphs (1) to (8) above or a pharmacologically acceptable salt thereof.

Paragraph 12. A connexin 26 inhibitor comprising a multimeric oleamide derivative represented by any one of formulas in Paragraphs (1) to (8) above or a pharmacologically acceptable salt thereof.

BRIEF DESCRIPTION OF DRAWINGS

In FIG. 8, "NT" denotes the result with respect to a group of mice with subcutaneous tumors that were not subjected to medicine administration or treatments.

DESCRIPTION OF THE PREFERRED EMBODIMENTS

Hereinafter, specific embodiments, technical scope, and other information about the present invention are described in detail.

[1] Bioactivities and Characteristics of Oleamide Derivatives of the Present Invention The present inventors synthesized multimeric oleamide derivatives that are represented by the above-mentioned formulas (1) to (8) by the methods described later in Examples, and they then examined whether each derivative had a connexin 26 inhibitory activity. As a result, the connexin 26 inhibitory activity was found in all the derivatives described above (see FIG. 3).

Figure 3:
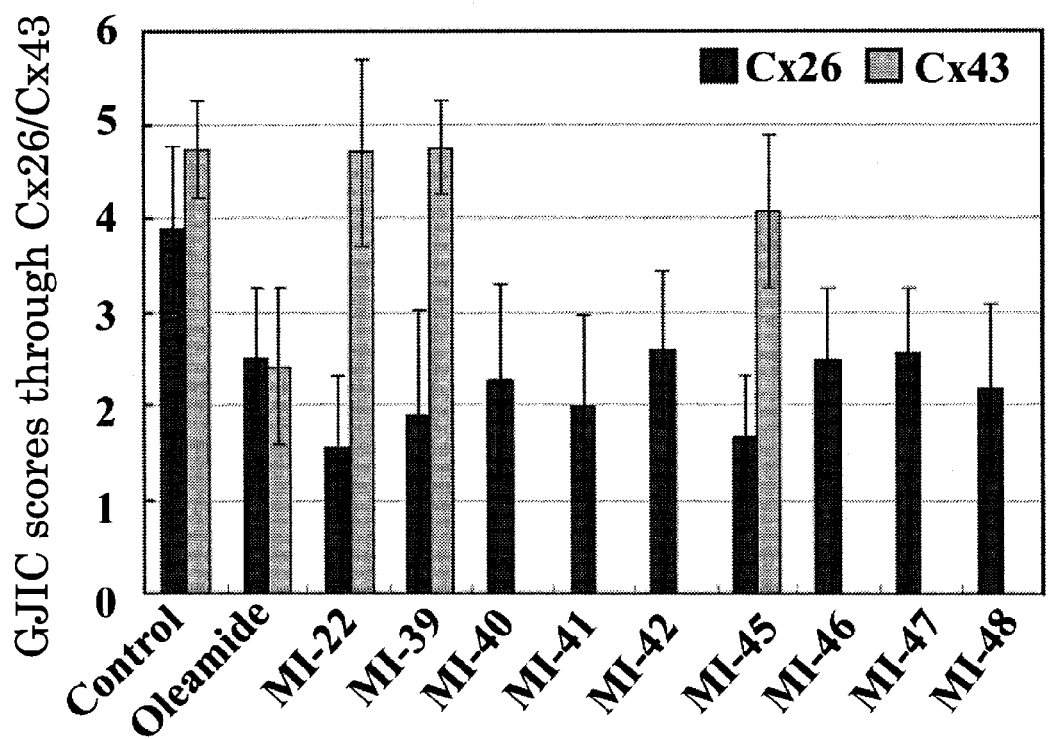
FIG. 3 is a graph showing the result of examining a connexin 26 inhibitory activity and a connexin 43 inhibitory activity of multimeric oleamide derivatives according to the present invention by the dye-transfer assay.

Among them, three dimer oleamide derivatives (MI-22, MI-39, and MI-45) that were found to have strong connexin 26 inhibitory activities were further examined to learn if they had connexin 43 inhibitory activities. As a result, these derivatives hardly inhibited the function of connexin 43, as shown in FIG. 3.

Among the connexin family, connexin 43 exists in central nerves or myocardial cells in a large amount. It is considered that an inhibition of the function thereof causes adverse effects, arrhythmia, for example. Therefore when oleamide derivatives are to be used for pharmaceutical development, it is desirable that they have characteristics that allow connexin 26 to be inhibited specifically without inhibiting the function of connexin 43. In this respect, MI-22 exhibited the most desirable result among the three oleamide derivatives described above. Thus the applicability of MI-22 to an anticancer spontaneous metastasis agent and an anticancer growth agent was studied.

Figure 7:
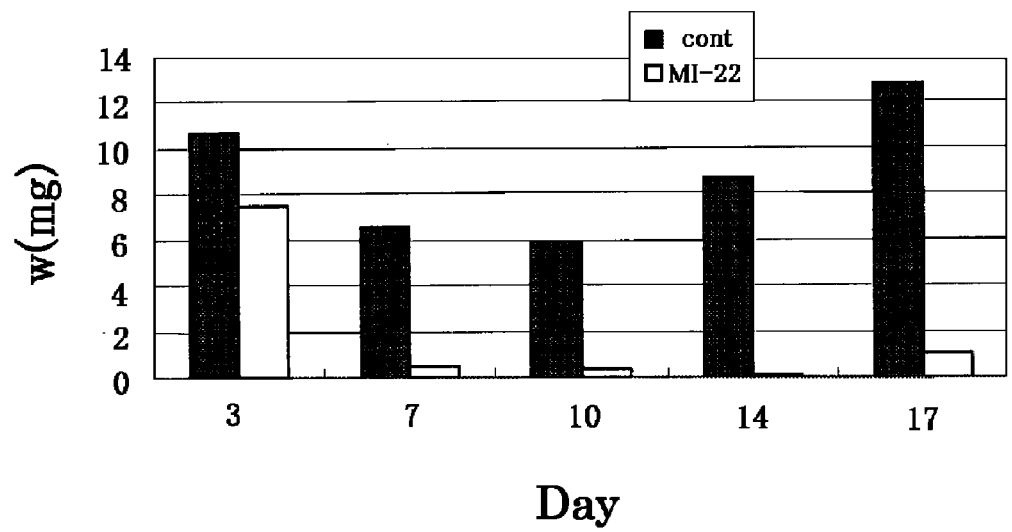
FIG. 7 is a graph indicating that the administration of MI-22 inhibits the growth of the Az521 cell, which is a human gastric cancer cell, in a nude mouse.

As a result, the aforementioned MI-22 conspicuously suppressed the spontaneous metastasis of cancer (FIGS. 4 and 5), and the ability to inhibit cancer growth (antitumor effect) also was found (FIG. 7). The details are described later in the Examples section.

The aforementioned MI-22 has the following characteristics and therefore is a suitable substance for the development of medicines such as an anticancer spontaneous metastasis agent and an anticancer growth agent.

(1) It has an excellent handling property, since it is an oily matter and dissolves well in an organic solvent.
(2) It exhibits a low gap junction intercellular communication (GJIC) score obtained through connexin 26, specifically 2 or lower, in the dye-transfer assay described later and thus strongly inhibits the function of connexin 26. On the other hand, the GJIC score obtained through connexin 43 was almost the same as that of a control and thus no effect of inhibiting connexin 43 was found (FIG. 3). Thus the development of safe medicines with fewer side effects such as arrhythmia can be expected.
(3) Cytotoxicity also is not found (FIG. 6) and therefore it is considered a biologically safe substance. In the experiment (Example 3) in which the inhibition of spontaneous metastasis of cancer by MI-22 was investigated, even when the mice were administered MI-22 every day, none died due to the administration of MI-22. MI-22 is thus also considered to be a highly safe substance.
(4) Generally, it is relatively stable because it has no epoxide structure that is decomposed easily under various conditions in, for example, acid, base, heat, light, and nucleophilic reaction. Moreover, it cannot react with a base, such as nucleic acid, to damage DNAs.
(5) The dimer structure of MI-22 is formed of a carbon chain, so it will not decompose to become oleamide, which is a monomer. Similarly, with respect to other oleamide derivatives of the present invention, since the multimeric structures thereof are also formed of carbon chains, they tend not to decompose and change easily. Thus they are easy to treat variously.

Moreover, it should be noted that the aforementioned MI-22 suppresses (inhibits) not experimental metastasis, but spontaneous metastasis of cancer. Conventional drug evaluations (evaluations of the cancer metastasis inhibitory activity) were carried out not through the implantation of cancer cells, but through experimental metastasis where cancer was allowed to metastasize experimentally. That is, the evaluation of effectiveness was made by injecting cancer cells intravenously and then judging whether cancer has metastasized to the lungs two weeks after an administration of a candidate medicine. On the contrary, in the examples described later the drug evaluation is made by implanting cancer cells and then judging whether cancer has metastasized later. This allows the effectiveness to be evaluated in a state close to that of actual cancer. In other words, the aforementioned MI-22 and the other oleamide derivatives of the present invention have a very high possibility of being used to develop effective drugs for cancer therapy as substances suppressing (inhibiting) the spontaneous metastasis of cancer that directly reflects cancer metastasis in vivo.

The oleamide derivatives of the present invention can be produced by a method described later in the Examples section. However, the production method is not limited thereto, but can be modified variously. If it is found that they exist naturally, the oleamide derivatives of the present invention can be isolated from a natural product and can then be purified, or they can be produced by using a substance obtained from a natural product as a raw material and allowing them to be subjected to treatments, such as reactions. If necessary, they can be those produced by the use of a biological material such as a microorganism.

Figure 1:
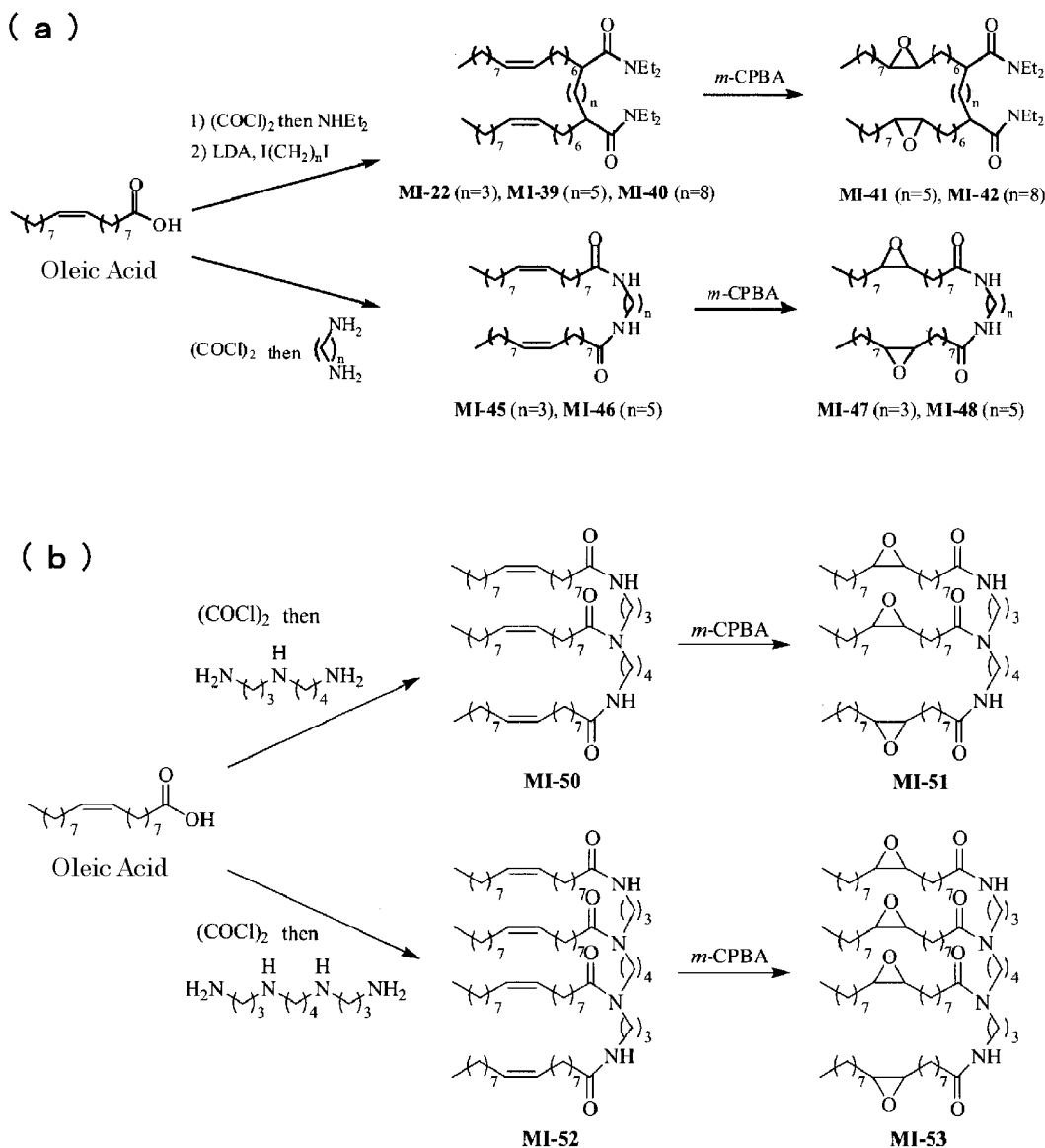
FIG. 1 shows schematic views illustrating methods of synthesizing multimeric oleamide derivatives according to the present invention, where (a) and (b) show methods of synthesizing dimer oleamide derivatives and trimer/tetramer oleamide derivatives, respectively.

When being produced by the processes shown in FIG. 1, they can be produced in fewer steps because the reaction of converting double bonds into oxirane can be omitted in the seven oleamide derivatives (MI-22, MI-39, MI-40, MI-45, MI-46, MI-50, and MI-52) that have double bonds (alkene) in the carbon chains thereof.

The oleamide derivatives of the present invention each have a connexin 26 inhibitory activity. In this context, the term "connexin 26 inhibitory activity" denotes that an administration of oleamide derivatives of the present invention suppresses the intercellular transfer of a substance that is mediated by connexin 26. This can be confirmed easily by examining the change in the GJIC score obtained through connexin 26 by the dye-transfer assay described later.

[2] Applications of Oleamide Derivatives of the Present Invention

As described above, since the oleamide derivatives of the present invention each exhibit a connexin 26 inhibitory activity, they can be used for research reagents as connexin 26 inhibitors. Further, since they have a bioactivity of specifically inhibiting connexin 26, which forms a gap junction as described above, they can also be expected to be used for developing medicines by utilizing this property.

Because the oleamide derivatives, such as the aforementioned MI-22, have a strong cancer metastasis inhibitory activity and antitumor activity, they can be used for raw materials of medicines such as anticancer agents (antitumor drugs), further supplements, and functional foods (food compositions) that have, for example, anticancer effects or cancer prevention effects.

The present invention embraces not only the oleamide derivatives described above, but also pharmacologically acceptable salts thereof. Examples of these pharmacologically acceptable salts include: hydrohalogenic acid salts, such as hydrofluoric acid salt and hydrochloride; inorganic acid salts, such as sulfate and nitrate; alkali metal salts, such as sodium salt and potassium salt; sulfonate; and organic acid salts.

When the oleamide derivatives of the present invention or pharmacologically acceptable salts thereof (hereinafter referred to simply as "oleamide derivatives") are used for developing medicines, in one embodiment, they can be used as a lead compound employed in the process of developing pharmaceuticals.

An example where an oleamide derivative of the present invention is used for a pharmaceutical (pharmaceutical composition) is explained. It can be administered to human (or animal) without modification or as a pharmaceutical composition to be prepared together with a conventional medicinal preparation carrier. The dosage form of the pharmaceutical composition is not particularly limited and can be selected suitably according to need. Examples of the dosage form include oral agents, such as tablets, capsules, granules, subtle granules, and powders, and also parenteral agents, such as injections, suppositories, and endermic liniments.

Oral agents, such as tablets, capsules, granules, subtle granules, and powders, are produced in the usual manner using, for example, starch, lactose, sucrose, trehalose, mannitol, carboxymethylcellulose, cornstarch, and inorganic salts. The amount of oleamide derivatives of the present invention to be contained in such preparations is not particularly limited and can be suitably set. For this type of preparation, for instance, a binder, disintegrator, surfactant, lubricant, fluidity promoter, corrigent, colorant, or flavor will be suitable.

In the case of parenteral agents, the dosage is adjusted according to the patient's age and weight and extent of the disease, among other things, and it is administered, for example, by intravenous injection, intravenous infusion, subcutaneous injection, or intramuscular injection. The parenteral agents can be produced in the usual manner. Generally, for instance, distilled water for injection and physiological saline can be used as a diluent. Furthermore, a disinfectant, an antiseptic, and a stabilizer can be added as required. From the viewpoint of stability, the parenteral agents can be prepared as follows. That is, after the dosage is put into a vial, it is frozen to remove moisture by a common freeze-drying process and can then be prepared again as a solution from the freeze-dried product immediately before use. Moreover, an isotonizing agent, a stabilizer, an antiseptic, and a soothing agent can be added, if necessary. The amount of oleamide derivatives of the present invention contained in these preparations is not particularly limited and can be set arbitrarily. Other examples of parenteral agents include solutions for external use, endermic liniments such as an ointment, and suppositories for intrarectal administration. These agents also can be produced in the usual manner.

A known drug delivery system (DDS) allows an oleamide derivative of the present invention to be enclosed in a carrier such as liposome to be administered in vivo. In this case, a carrier that specifically recognizes a target site (a cancer cell, for example) allows efficient delivery of the oleamide derivative of the present invention to the target site and is therefore effective.

Furthermore, as described above, the oleamide derivatives of the present invention can also be used for foods (food compositions) such as supplements and functional foods. That is, they can be added to foods and drinks as raw materials of various processed foods or various drinks, or they can be processed into pellets, tablets, and granules, for example, with an excipient such as dextrin, lactose, starch, flavoring, or dye, or coated with, for instance, gelatin to be processed into capsules and thereby can be used, for example, as health foods and supplement foods.

EXAMPLES

Hereinafter, examples of the present invention are described, but the present invention is not limited by them.

Example 1

Synthesis of Multimeric Oleamide Derivatives According to the Present Invention

First, the methods of synthesizing multimeric oleamide derivatives of the present invention, including MI-22, are described. FIG. 1(a) schematically shows a chemical synthesis of dimer oleamide derivatives, and FIG. 1(b) schematically shows one of trimer/tetramer oleamide derivatives.

In the following examples, the nuclear magnetic resonance ($^1$H-NMR) spectra were measured at a temperature of 20° C. to 25° C. at 300 MHz, with tetramethylsilane being used as an internal standard. The infrared (IR) absorption spectrum was measured by a diffuse reflectance method using KBr as a diluent. The adsorbent used for column chromatography was E. Merck silica gel 60, and E. Merck precoated TLC plates and silica gel $F_{254}$ were used for the thin-layer chromatography.

[1.1] Synthesis of MI-22

MI-22, i.e., $N^1,N^1,N^7,N^7$-Tetraethyl-2,6-di[(Z)-7-hexadecenyl]-heptanediamide, was synthesized by the following method.

In a nitrogen atmosphere, oxalyl chloride (0.46 mL, 5.4 mmol) was dropped into an absolute methylene chloride solution (8.5 mL) of oleic acid (503 mg, 1.8 mmol) under ice cooling. The solution was then stirred at room temperature for four hours. Thereafter it was concentrated under reduced pressure. Diethylamine (1.0 mL, 9.7 mmol) was added to the resultant residue, which was then stirred at room temperature for 0.5 hour. Water was then added, and extraction was performed with ethyl acetate. The organic layer thus obtained was washed with saturated saline, dried with anhydrous sodium sulfate, and concentrated under reduced pressure. The crude extract thus obtained was purified using column chromatography (n-hexane:ethyl acetate=1:2). Thus (Z)-N, N-diethyl-9-octadecenamide (495 mg, 82%) was obtained as a colorless oily matter.

The nuclear magnetic resonance ($^1$H-NMR) spectral data of the above-mentioned colorless oily matter is indicated below:

$^1$H NMR (CDCl$_3$, 300 MHz): δ 0.88 (3H, t, J=6.6 Hz), 1.11 (3H, t, J=7.2 Hz), 1.17 (3H, t, J=7.2 Hz), 1.25-1.39 (20H, m), 1.50-1.75 (2H, m), 1.95-2.10 (4H, m), 2.28 (2H, t, J=7.4 Hz), 3.30 (2H, q, J=6.6 Hz), 3.37 (2H, q, J=6.6 Hz), 5.32-5.36 (2H, m).

A THF solution (12 mL) of the above-mentioned colorless oily matter (153 mg, 0.45 mmol) was cooled to −40° C., and LDA (0.7 mL, 1.4 mmol) was then added. This was stirred at −40° C. for 0.5 hour. Thereafter 1,3-diiodopropane (0.26 mL, 2.3 mmol) was added thereto, which was then stirred at −40° C. for three hours. After that, a saturated ammonium chloride aqueous solution was added. Subsequently, the organic layer was separated and an aqueous layer was extracted with ethyl acetate. The mixed organic layer was washed with saturated saline, dried with anhydrous sodium sulfate, and concentrated under reduced pressure. The crude extract thus obtained was purified using column chromatography (n-hexane:ethyl acetate=4:1). Thus MI-22 (22 mg, 21%) was obtained as a colorless oily matter.

The respective data of the infrared (IR) absorption spectrum, the nuclear magnetic resonance ($^1$H, $^{13}$C-NMR) spectrum, and the mass spectrometry (FAB) of the MI-22 are indicated below:

IR (KBr) 3416, 2855, 1614 cm$^{-1}$;

$^1$H NMR (CDCl$_3$, 300 MHz): δ 0.88 (6H, t, J=6.4 Hz), 1.09 (6H, t, J=7.2 Hz), 1.14 (6H, t, J=7.2 Hz), 1.20-1.38 (48H, m), 1.50-1.62 (2H, m), 1.98-2.03 (8H, m), 2.42-2.52 (2H, m), 3.31 (4H, q, J=7.2 Hz), 3.36 (4H, q, J=7.2 Hz), 5.32-5.35 (4H, m);

$^{13}$C NMR (CDCl$_3$, 300 MHz): δ 12.9, 13.9, 14.8, 22.5 (2C), 27.0 (2C), 27.4, 29.0 (3C), 29.3, 29.6 (2C), 31.7 (2C), 33.3, 33.5, 40.2, 41.0, 41.6, 129.5, 129.7, 175.1; and LRMS (FAB) m/z 716 (MH$^+$). HRMS (FAB) calcd for C$_{47}$H$_{91}$N$_2$O$_2$, 715.7081; found, 715.7078.

[1.2] Synthesis of MI-39

MI-39, i.e., N$^1$,N$^1$,N$^9$,N$^9$-Tetraethyl-2,8-di[(Z)-7-hexadecenyl]nonanediamide, was synthesized by the following method.

In the same manner as in the synthesis of MI-22 described above, LDA (0.34 mL, 0.66 mmol) was added to a THF solution of (Z)-N,N-diethyl-9-octadecenamide (70 mg, 0.22 mmol). This was stirred at −40° C. for 0.5 hour. Thereafter 1,5-diiodopentane (3.0 mL, 0.17 mmol) was added, which was then stirred at −40° C. for three hours. After that, a saturated ammonium chloride aqueous solution was added. Subsequently, the organic layer was separated and an aqueous layer was extracted with ethyl acetate. The mixed organic layer was washed with saturated saline, dried with anhydrous sodium sulfate, and concentrated under reduced pressure. The crude extract thus obtained was purified using column chromatography (n-hexane:ethyl acetate=8:1). Thus MI-39 (50 mg, 30%) was obtained as a colorless oily matter.

The respective data of the nuclear magnetic resonance ($^1$H-NMR) spectrum and the mass spectrometry (FAB) of the MI-39 are indicated below:

$^1$H NMR (CDCl$_3$, 300 MHz): δ 0.88 (6H, t, J=6.4 Hz), 1.07-1.29 (64H, m), 1.50-1.62 (2H, m), 1.99-2.01 (8H, m), 2.28 (2H, m), 3.35 (8H, q, J=5.4 Hz), 5.33 (4H, m); and LRMS (FAB) m/z 744 (MH$^+$). HRMS (FAB) calcd for C$_{49}$H$_{95}$N$_2$O$_2$, 743.7394; found, 743.7415.

[1.3] Synthesis of MI-40

MI-40, i.e., N$^1$,N$^1$,N$^{12}$,N$^{12}$-Tetraethyl-2,11-di[(Z)-9-hexadecenyl]dodecanediamide, was synthesized by the following method.

In the same manner as in the synthesis of MI-22 described above, LDA (0.25 mL, 0.51 mmol) was added to a THF solution of (Z)-N,N-diethyl-9-octadecenamide (52 mg, 0.17 mmol). This was stirred at −40° C. for 0.5 hour. Thereafter 1,5-diiodooctane (0.17 mL, 0.85 mmol) was added, which was then stirred at −40° C. for three hours. After that, a saturated ammonium chloride aqueous solution was added. Subsequently, the organic layer was separated and an aqueous layer was extracted with ethyl acetate. The mixed organic layer was washed with saturated saline, dried with anhydrous sodium sulfate, and concentrated under reduced pressure. The crude extract thus obtained was purified using column chromatography (n-hexane:ethyl acetate=8:1). Thus MI-40 (21 mg, 16%) was obtained as a colorless oily matter.

The respective data of the nuclear magnetic resonance ($^1$H-NMR) spectrum and the mass spectrometry (FAB) of the MI-40 are indicated below:

$^1$H NMR (CDCl$_3$, 300 MHz): δ 0.88 (6H, t, J=6.4 Hz), 1.08-1.59 (72H, m), 1.99-2.04 (8H, m), 2.50 (2H, m), 3.35 (8H, q, J=5.4 Hz), 5.33 (4H, m); and LRMS (FAB) m/z 786 (MH$^+$). HRMS (FAB) calcd for C$_{52}$H$_{101}$N$_2$O$_2$, 785.7863; found, 785.7897.

[1.4] Synthesis of MI-45

MI-45, i.e., N$^1$-[(Z)-3-Octadec-9-enoylaminopropyl]-(Z)-9octadecenamide, was synthesized by the following method.

In a nitrogen atmosphere, oxalyl chloride (0.11 mL, 1.2 mmol) was dropped into an absolute methylene chloride solution (3.0 mL) of oleic acid (100 mg, 0.35 mmol) under ice cooling. The solution was then stirred at room temperature for four hours. Thereafter it was concentrated under reduced pressure. Propane-1,3-diamine (0.015 mL, 0.18 mmol) was added to the resultant residue, which was then stirred at room temperature for one hour. Water was then added, and extraction was performed with ethyl acetate. The organic layer thus obtained was washed with saturated saline, dried with anhydrous sodium sulfate, and concentrated under reduced pressure. The crude extract thus obtained was purified using column chromatography (n-hexane:ethyl acetate=1:4). Thus MI-45 (89 mg, 84%) was obtained as a colorless oily matter.

The respective data of the nuclear magnetic resonance ($^1$H-NMR) spectrum and the mass spectrometry (FAB) of the above-mentioned MI-45 are indicated below:

$^1$H NMR (CDCl$_3$, 300 MHz): δ 0.88 (6H, t, J=6.6 Hz), 1.27-1.31 (40H, m), 1.57-1.61 (6H, m), 1.98-2.05 (8H, m), 2.20 (4H, dd, J=7.4 Hz), 3.27 (4H, dd, J=12.4, 5.9 Hz), 5.34 (4H, m), 6.19 (2H, brs); and LRMS (FAB) m/z 604 (MH$^+$). HRMS (FAB) calcd for C$_{39}$H$_{75}$N$_2$O$_2$, 603.5829; found, 603.5813.

[1.5] Synthesis of MI-46

MI-46, i.e., $N^1$-[(Z)-5-Octadec-9-enoylaminopentyl]-(Z)-9-Octadecenamide, was synthesized by the following method.

In the same manner as in the synthesis of MI-45, oxalyl chloride (0.14 mL, 1.58 mmol) was dropped into an absolute methylene chloride solution of oleic acid (127 mg, 0.45 mmol) under ice cooling. The solution was then stirred at room temperature for four hours. Thereafter it was concentrated under reduced pressure. Pentane-1,5-diamine (0.026 mL, 0.22 mmol) was added to the resultant residue, which was then stirred at room temperature for one hour. Water was then added, and extraction was performed with ethyl acetate. The organic layer thus obtained was washed with saturated saline, dried with anhydrous sodium sulfate, and concentrated under reduced pressure. The crude extract thus obtained was purified using column chromatography (dichloromethane:methanol=20:1). Thus MI-46 (127 mg, 45%) was obtained as a colorless oily matter.

The respective data of the nuclear magnetic resonance ($^1$H-NMR) spectrum and the mass spectrometry (FAB) of the above-mentioned MI-46 are indicated below:

$^1$H NMR (CDCl$_3$, 300 MHz): δ 0.85 (6H, t, J=6.5 Hz), 1.25-1.64 (42H, m), 1.97-2.01 (8H, m), 2.13-2.19 (4H, dd, J=7.2 Hz), 3.23 (4H, dd, J=12.4, 5.9 Hz), 5.27-5.40 (4H, m), 5.88 (2H, brs); and LRMS (FAB) m/z 631 (MH$^+$). HRMS (FAB) calcd for $C_{41}H_{78}N_2O_2$, 631.6142; found, 631.6130.

[1.6] Synthesis of MI-50

MI-50, i.e., $N^1$-{(Z)-3-Octadec-9-enoyl-N-[(Z)-4-octadec-9-enoylaminobutyl]-aminopropyl}-(Z)-9-octadecenamide, was synthesized by the following method.

In the same manner as in the synthesis of MI-45, oxalyl chloride (0.11 mL, 1.2 mmol) was dropped into an absolute methylene chloride solution of oleic acid (100 mg, 0.35 mmol) under ice cooling. The solution was then stirred at room temperature for four hours. Thereafter it was concentrated under reduced pressure. Spermidine (0.020 mL, 0.12 mmol) was added to the resultant residue, which was then stirred at room temperature for one hour. Water was then added, and extraction was performed with ethyl acetate. The organic layer thus obtained was washed with saturated saline, dried with anhydrous sodium sulfate, and concentrated under reduced pressure. The crude extract thus obtained was purified using column chromatography (dichloromethane:methanol=20:1). Thus MI-50 (75 mg, 23%) was obtained as a colorless oily matter.

The respective data of the nuclear magnetic resonance ($^1$H-NMR) spectrum and the mass spectrometry (FAB) of the above-mentioned MI-50 are indicated below:

$^1$H NMR (CDCl$_3$, 300 MHz): δ 0.88 (9H, t, J=6.5 Hz), 1.27-1.80 (72H, m), 1.99-2.01 (12H, m), 2.14-2.36 (6H, m), 3.11-3.42 (8H, m), 5.28-5.40 (6H, m); and LRMS (FAB) m/z 939 (MH$^+$). HRMS (FAB) calcd for $C_{61}H_{116}N_3O_3$, 938.9017; found, 938.9005.

[1.7] Synthesis of MI-52

MI-52, i.e., $N^1$-{(Z)-3-Octadec-9-enoyl-N-[(Z)-4-octadec-9-enoyl-N-{(Z)-3-octadec-9-enoylaminopropyl}-aminobutyl]-aminopropyl}-(Z)-9-octadecenamide, was synthesized by the following method.

In the same manner as in the synthesis of MI-45, oxalyl chloride (0.11 mL, 1.2 mmol) was dropped into an absolute methylene chloride solution of oleic acid (100 mg, 0.35 mmol) under ice cooling. The solution was then stirred at room temperature for four hours. Thereafter it was concentrated under reduced pressure. N,N$^1$-bis(3-aminopropyl)-1,4-butanediamine (18.2 mg, 0.086 mmol) was added to the resultant residue, which was then stirred at room temperature for one hour. Water was then added, and extraction was performed with ethyl acetate. The organic layer thus obtained was washed with saturated saline, dried with anhydrous sodium sulfate, and concentrated under reduced pressure. The crude extract thus obtained was purified using column chromatography (dichloromethane:methanol=20:1). Thus MI-52 (71 mg, 16%) was obtained as a colorless oily matter.

The respective data of the nuclear magnetic resonance ($^1$H-NMR) spectrum and the mass spectrometry (FAB) of the above-mentioned MI-52 are indicated below:

$^1$H NMR (CDCl$_3$, 300 MHz): δ 0.88 (12H, t, J=6.5 Hz), 1.27-1.77 (96H, m), 1.99-2.02 (16H, m), 2.16-2.37 (8H, m), 3.14-3.41 (12H, m), 5.28-5.30 (8H, m); and LRMS (FAB) m/z 1260 (MH$^+$). HRMS (FAB) calcd for $C_{68}H_{155}N_4O_4$, 1260.2048; found, 1260.2062.

[1.8] Synthesis of MI-41

MI-41, i.e., $N^1$,$N^1$,$N^9$,$N^9$-Tetraethyl-2,8-di[8-{(2S*,3R*)-3-octyl-oxiranyl}-octyl]nonanediamide, was synthesized by the following method.

M-chloroperbenzoic acid (28 mg, 0.13 mmol) was added to a dichloromethane solution (3 mL) of the aforementioned MI-39 (50 mg, 0.064 mmol) under ice cooling. The solution was stirred at room temperature for three hours. Thereafter a saturated sodium thiosulfate aqueous solution was added. The organic layer was then separated and an aqueous layer extracted with dichloromethane. The mixed organic layer was washed with saturated saline, dried with anhydrous sodium sulfate, and concentrated under reduced pressure. The crude extract thus obtained was purified by the use of column chromatography (n-hexane:ethyl acetate=3:1). Thus MI-41 (39 mg, 76%) was obtained as a white solid.

The respective data of the nuclear magnetic resonance ($^1$H-NMR) spectrum and the mass spectrometry (FAB) of the above-mentioned MI-41 are indicated below:

$^1$H NMR (CDCl$_3$, 300 MHz): δ 0.88 (6H, t, J=6.4 Hz), 1.08-1.64 (78H, m), 2.44-2.53 (2H, m), 2.89 (4H, brs), 3.36 (8H, q, J=7.2 Hz); and LRMS (FAB) m/z 776 (MH$^+$). HRMS (FAB) calcd for $C_{49}H_{95}N_2O_4$, 775.7292; found, 775.7323.

[1.9] Synthesis of MI-42

MI-42, i.e., $N^1$,$N^1$,$N^{12}$,$N^{12}$-Tetraethyl-2,11-di[8-{(2S*,3R*)-3-octyl-oxiranyl)-octyl]dodecanediamide, was synthesized by the following method.

M-chloroperbenzoic acid (21 mg, 0.095 mmol) was added to a dichloromethane solution of the aforementioned MI-40 (30 mg, 0.038 mmol) under ice cooling. The solution was stirred at room temperature for three hours. Thereafter a saturated sodium thiosulfate aqueous solution was added. The organic layer was then separated and an aqueous layer extracted with dichloromethane. The mixed organic layer was washed with saturated saline, dried with anhydrous sodium sulfate, and concentrated under reduced pressure. The crude extract thus obtained was purified by the use of column chromatography (n-hexane:ethyl acetate=4:1). Thus MI-42 (25 mg, 81%) was obtained as a colorless oily matter.

The respective data of the nuclear magnetic resonance ($^1$H-NMR) spectrum and the mass spectrometry (FAB) of the above-mentioned MI-42 are indicated below:

$^1$H NMR (CDCl$_3$, 300 MHz): δ 0.88 (6H, t, J=6.4 Hz), 1.08-1.64 (80H, m), 2.45-2.53 (2H, m), 2.89 (4H, brs), 3.36 (8H, q, J=7.2 Hz); and LRMS (FAB) m/z 818 (MH$^+$). HRMS (FAB) calcd for $C_{52}H_{101}N_2O_4$, 817.7761; found, 817.7729.

[1.10] Synthesis of MI-47

MI-47, i.e., $N^1$-[3-{8-[(2S*,3R*)-3-Octyl-oxiranyl]-octanoylamino}-propyl]-{8-(2S*,3R*)-3-octyl-oxiranyl}octanamide, was synthesized by the following method.

M-chloroperbenzoic acid (100 mg, 0.45 mmol) was added to a dichloromethane solution of the aforementioned MI-45 (60 mg, 0.10 mmol) under ice cooling. The solution was stirred at room temperature for three hours. Thereafter a saturated sodium thiosulfate aqueous solution was added. The organic layer was then separated and an aqueous layer extracted with dichloromethane. The mixed organic layer was washed with saturated saline, dried with anhydrous sodium sulfate, and concentrated under reduced pressure. The crude extract thus obtained was purified by the use of column chromatography (ethyl acetate). Thus MI-47 (60 mg, 94%) was obtained as a colorless oily matter.

The respective data of the nuclear magnetic resonance ($^1$H-NMR) spectrum and the mass spectrometry (FAB) of the above-mentioned MI-47 are indicated below:

$^1$H NMR (CDCl$_3$, 300 MHz): δ 0.88 (6H, t, J=6.5 Hz), 1.25-1.76 (54H, m), 2.20 (4H, t, J=7.5 Hz), 3.01 (4H, brs), 3.27 (4H, q, J=6.4 Hz), 6.49 (2H, brs); and LRMS (FAB) m/z 636 (MH$^+$). HRMS (FAB) calcd for $C_{39}H_{75}N_2O_4$, 635.5727; found, 635.5726.

[1.11] Synthesis of MI-48

MI-48, i.e., $N^1$-[3-{8-[(2S*,3R*)-3-Octyl-oxiranyl]-octanoylamino}-propyl]-{8-(2S*,3R*)-3-octyl-oxiranyl}octanamide, was synthesized by the following method.

M-chloroperbenzoic acid (78 mg, 0.35 mmol) was added to a dichloromethane solution of the aforementioned MI-46 (63 mg, 0.10 mmol) under ice cooling. The solution was stirred at room temperature for three hours. Thereafter a saturated sodium thiosulfate aqueous solution was added. The organic layer was then separated and an aqueous layer extracted with dichloromethane. The mixed organic layer was washed with saturated saline, dried with anhydrous sodium sulfate, and concentrated under reduced pressure. The crude extract thus obtained was purified by the use of column chromatography (dichloromethane:methanol=20:1). Thus MI-48 (66 mg, 99%) was obtained as a colorless oily matter.

The respective data of the nuclear magnetic resonance ($^1$H-NMR) spectrum and the mass spectrometry (FAB) of the above-mentioned MI-48 are indicated below:

$^1$H NMR (CDCl$_3$, 300 MHz): δ 0.88 (6H, t, J=6.5 Hz), 1.25-1.73 (58H, m), 2.17 (4H, t, J=7.5 Hz), 2.90 (4H, brs), 3.24 (4H, q, J=6.4 Hz), 5.70 (2H, brs); and LRMS (FAB) m/z 664 (MH$^+$). HRMS (FAB) calcd for $C_{41}H_{79}N_2O_4$, 663.6040; found, 660.6050.

[1.12] Synthesis of MI-51

MI-51, i.e., $N^1$-{3-[8-{(2S*,3R*)-3-Octyl-oxiranyl}-octanoyl]-N-[4-{8[(2S*,3R*)-3-octyl-oxiranyl]-octanoylamino}-butyl]-aminopropyl}-{8-(2S*,3R*)-3-octyl-oxiranyl}octanamide, was synthesized by the following method.

M-chloroperbenzoic acid (30 mg, 0.19 mmol) was added to a dichloromethane solution of the aforementioned MI-50 (36 mg, 0.038 mmol) under ice cooling. The solution was stirred at room temperature for three hours. Thereafter a saturated sodium thiosulfate aqueous solution was added. The organic layer was then separated and an aqueous layer extracted with dichloromethane. The mixed organic layer was washed with saturated saline, dried with anhydrous sodium sulfate, and concentrated under reduced pressure. The crude extract thus obtained was purified by the use of column chromatography (dichloromethane:methanol=20:1). Thus MI-51 (38 mg, 100%) was obtained as a colorless oily matter.

The respective data of the nuclear magnetic resonance ($^1$H-NMR) spectrum and the mass spectrometry (FAB) of the above-mentioned MI-51 are indicated below:

$^1$H NMR (CDCl$_3$, 300 MHz): δ 0.88 (9H, t, J=6.5 Hz), 1.26-1.77 (84H, m), 2.14-2.36 (6H, m), 2.89-2.91 (6H, m), 3.07-3.42 (8H, m), 5.31 (1H, brs), 6.88 (1H, brs); and LRMS (FAB) m/z 987 (MH$^+$). HRMS (FAB) calcd for $C_{61}H_{116}N_3O_6$, 986.8864; found, 986.8820.

[1.13] Synthesis of MI-53

MI-53, i.e., $N^1$-(3-{[8-{(2S*,3R*)-3-Octyl-oxiranyl}-octanoyl]-[4-({8-[(2S*,3R*)-3-octyl-oxiranyl]-octanoyl}-N-{3-[8-{(2S*,3R*)-3-octyl-oxiranyl}-octanoylamino]-propyl}-amino)-butyl]-amino}-propyl)-8-{(2S*,3R*)-3-octyl-oxiranyl}octanamide, was synthesized by the following method.

M-chloroperbenzoic acid (32 mg, 0.14 mmol) was added to a dichloromethane solution of the aforementioned MI-52 (36 mg, 0.029 mmol) under ice cooling. The solution was stirred at room temperature for three hours. Thereafter a saturated sodium thiosulfate aqueous solution was added. The organic layer was then separated and an aqueous layer extracted with dichloromethane. The mixed organic layer was washed with saturated saline, dried with anhydrous sodium sulfate, and concentrated under reduced pressure. The crude extract thus obtained was purified by the use of column chromatography (dichloromethane:methanol=20:1). Thus MI-53 (36 mg, 94%) was obtained as a colorless oily matter.

The respective data of the nuclear magnetic resonance ($^1$H-NMR) spectrum and the mass spectrometry (FAB) of the above-mentioned MI-53 are indicated below:

$^1$H NMR (CDCl$_3$, 300 MHz): δ 0.88 (12H, t, J=6.5 Hz), 1.11-1.77 (112H, m), 2.15-2.66 (8H, m), 3.01-3.02 (8H, m), 3.09-3.41 (12H, m), 6.81 (1H, brs), 6.93 (1H, brs); and LRMS (FAB) m/z 1324 (MH$^+$). HRMS (FAB) calcd for $C_{82}H_{155}N_4O_8$, 1324.1845; found, 1324.1849.

Example 2

Connexin 26-Specific Inhibition of the Aforementioned Multimeric Oleamide Derivatives Next, with respect to each oleamide derivative synthesized by the method described above, we studied whether each derivative inhibited connexin 26 (in other words, whether each one inhibited the transfer of a substance from one cell to another through a gap junction formed by the connexin 26). The experimental method was the same as that described in International Publication WO 2004/060398. Each gap junction intercellular communication (GJIC) score of each test substance was evaluated by dye-transfer assay.

[2.1] Cell Strain and Cell Culture

In the same manner as in the method described in the above-mentioned publication, human uterocervical squamaous carcinoma cells (HeLa cells) were used for the experiment. More specifically, HeLa cell subclones (HeLa-Cx26 and HeLa-Cx43) were used, and they stably expressed rat connexin 26 (Cx26) and rat connexin 43 (Cx43), respectively. All cells (including those in the examples described later) were incubated in Dulbecco's modified eagle's medium (DMEM) with 10% fetal calf serum (FCS) added.

[2.2] Dye-transfer Assay

A day before the assay, the HeLa-Cx26 and HeLa-Cx43 cells each were suspended individually in DMEM containing 10% FCS. The respective cells were divided to be cultured as donor cells and recipient cells. The recipient cells were cultured in a culture dish with a diameter of 3 cm and were adjusted to yield subconfluent monolayers at the time of assay.

In the assay, first, both the dyes of calcein (gap junction-permeable) and DiI (gap junction-impermeable) were added to the culture of donor cells at concentrations of 10 µM and 2 µM, respectively, and incubated for one hour. Double-labeled donor cells were trypsinized and washed three times with phosphate-buffered saline. Thereafter each single donor cell was overlaid gently on unlabeled recipient cells. It took one hour for the donor cell to settle over a monolayer. Then it started to exhibit dye coupling in about 1.5 hours. Dye transfer from a donor cell to an adjacent recipient cell through a gap junction was observed.

Figure 2:
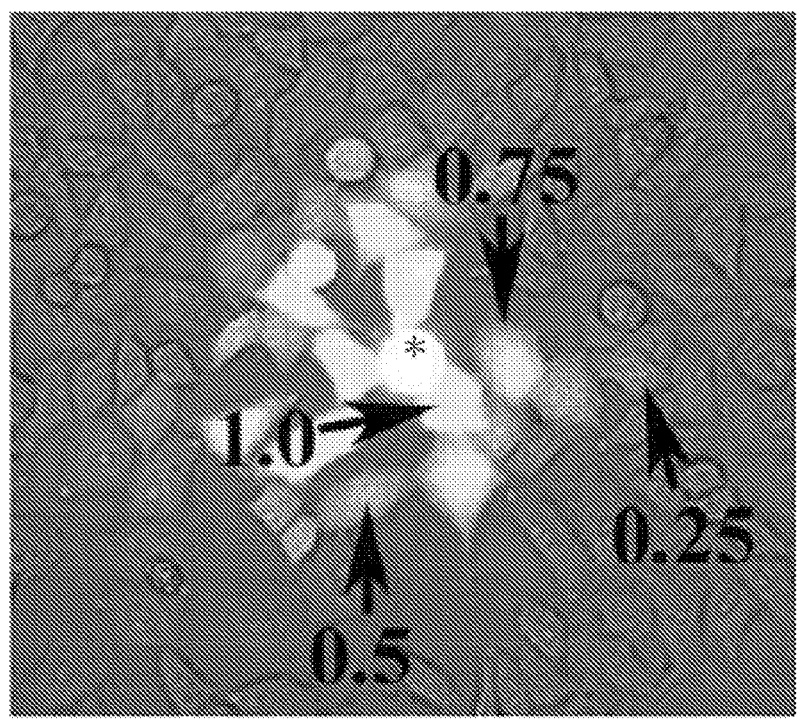
FIG. 2 is a photograph showing an example of microphotographs observed by dye-transfer assay.

In order to evaluate the inhibitory activity of each test substance with respect to the dye-coupling, one hour after the donor cells were planted, oleamide and the multimeric oleamide derivatives described above each were dissolved in ethanol, and 10 µL thereof was then added to each culture dish so that the final concentration was 20 µM. For control, ethanol diluted 1000 times was added to a culture dish. One hour after that, each culture dish was observed with a confocal scanning microscope (LSM510). FIG. 2 shows an example of the microphotography thus taken.

In FIG. 2, since the donor cell indicated with a "*" mark contains both the calcein (green fluorescence) and DiI (red fluorescence), it is shown in yellow in the original drawing. Furthermore, when gap junction-permeable calcein is transferred to a recipient cell through a gap junction by the dye coupling, this cell is shown in green. With such an assay, the GJIC score of each test substance is evaluated as follows.

That is, the evaluation was made as "0" where no dye-coupling of a donor cell is found, "1" where the dye-coupling of a donor cell to an adjacent recipient cell is found, "2" and "3" in cases where calcein that has been transferred to the adjacent recipient cell is transferred to the second and third adjacent cells in a direction away from the donor cell, respectively, and so on. Also, as shown with arrows in the drawing, the extent of cell dyeing was evaluated with four levels of 0.25, 0.5, 0.75, and 1.0 as intermediate levels.

Such an assay was carried out three times repeatedly. At least 30 donor cells were used to evaluate each test substance. Then the average value and standard deviation of the GJIC scores of the respective test substances were calculated. FIG. 3 shows a graph indicating the results of this assay and the GJIC scores of the respective oleamide derivatives. In the graph, the black bars each indicate a GJIC score obtained through connexin 26, and the gray bars each indicate a GJIC score obtained through connexin 43. With respect to the GJIC scores obtained through connexin 26, all the dimer oleamide derivatives to be used for the experiment showed a similar value to or a lower value than that of oleamide. Thus they were found to have a connexin 26 inhibitory activity.

Similarly, with respect to the trimer oleamide derivatives (MI-60 and MI-61) as well as the tetramer oleamide derivatives (MI-52 and MI-53), they were found to have a connexin 26 inhibitory activity as compared to the control by visual observation in the above-mentioned assay.

The three dimer oleamide derivatives (MI-22, MI-39, and MI-45) that were found to have a strong connexin 26 inhibitory activity in the assay described above showed no connexin 43 inhibitory activity, as shown in the drawing. That is, these oleamide derivatives inhibited connexin 26 specifically, but did not inhibit connexin 43. Thus in terms of the property that allows them to inhibit connexin 26 specifically without inhibiting connexin 43, MI-22 showed the best results among the three oleamide derivatives described above. Therefore the analysis was performed using the MI-22 in the following.

Example 3

Inhibition of Spontaneous Metastasis of Cancer by MI-22, Described Above

With the following experiment, it was examined whether MI-22 having a connexin 26 inhibitory activity as described above practically inhibited spontaneous metastasis of cancer in an animal.

[3.1] Method

The experiment was carried out by the same method as that described in International Publication WO 2004/060398. That is, after subcutaneously inoculating $1 \times 10^5$ BL6 cells (substrains of B16 mouse melanoma cells) to a planter of each 4-week-old C57BL/6 mouse, the mice were classified into two groups.

(1) MI-22 administration group: a group of mice subjected to intraperitoneal injection of MI-22 (10 mg) dissolved in olive oil (10 mL) so as to be 0.01 mL per 1 g of the weight of a mouse, once a day (about 0.2 mL per administration) on consecutive days (2) Nontreatment (Nt) group: a group of mice subjected to no drug administration/treatment by injection.

This treatment was carried out on consecutive days from the next day of the BL6 cells inoculation. When tumors that had formed at the inoculation sites grew to have diameters of about 7 mm, the legs with the tumors were removed by amputation at the knee joints. Then the above-mentioned treatment was carried out for another two days after the amputation. Thereafter the mice were fed without being treated. Four weeks after the amputations at the knee joints, the mice were euthanized, and metastasized tubercles that had formed at the pleura surface in the left and right lungs (the number of foci that metastasized to the lungs) were counted visually. An evaluation was made using 15 mice per each group.

[3.2] Results

Figure 4:
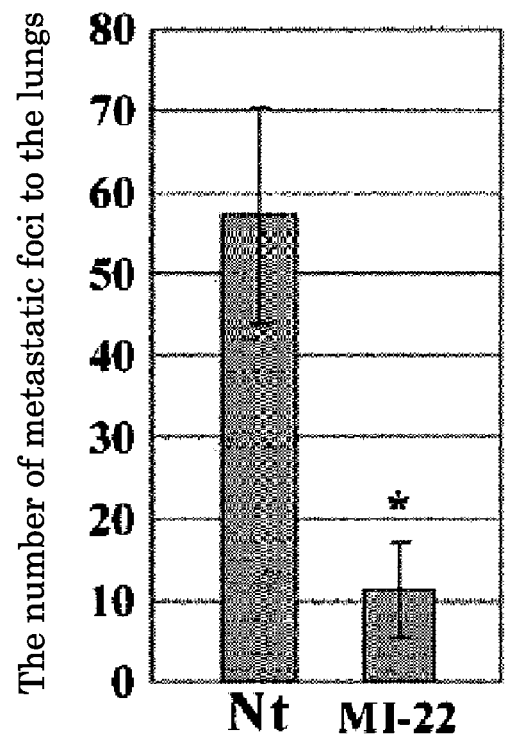
FIG. 4 is a graph showing the result of examining whether spontaneous metastasis of cancer was inhibited through the administration of MI-22.
Figure 5:
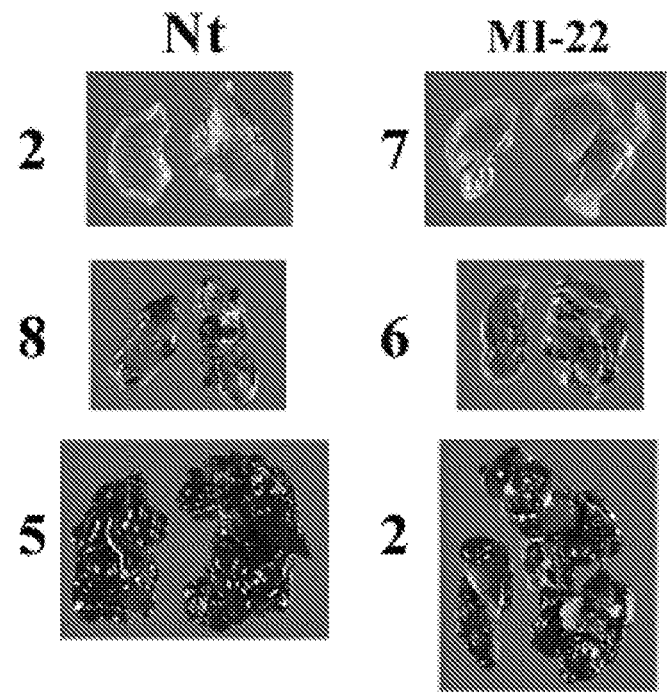
FIG. 5 shows the levels of metastasis of a mouse melanoma BL6 cell into the lungs of a mouse through the administration of MI-22. The metastasis is divided into three levels, i.e., none (upper row), moderate (middle row), and frequent (lower row). The photographs show the typical lungs of mice observed on dissection. The numerical values each indicate the number of mice with each level of lung metastasis.

FIGS. 4 and 5 show the results of the above-mentioned experiment. In the graph shown in FIG. 4, the vertical axis indicates the number of foci that had metastasized to the lungs. It showed that in the MI-22 administration group, the number of metastatic foci decreased by 80%, and thereby MI-22 inhibited/suppressed spontaneous metastasis of cancer conspicuously as compared to the nontreatment (Nt) group.

FIG. 5 shows, for example, photographs of lungs extirpated from each mouse of the MI-22 administration group and the nontreatment (Nt) group. That is, the upper panels show lungs with no spontaneous metastasis of cancer and the number of mice having such lungs; the middle panels show lungs with slight spontaneous metastasis, and the number of mice having such lungs; and the lower panels show lungs with considerable spontaneous metastasis and the number of mice having such lungs. In the nontreatment (Nt) group, the numbers of lungs with no spontaneous metastasis of cancer, with slight spontaneous metastasis, and with considerable spontaneous metastasis are two, eight, and five. On the other hand, they are seven, six, and two in the MI-22 administration group, respectively. Similarly, from this result it was proved that MI-22 inhibited and strongly suppressed spontaneous metastasis of cancer.

Furthermore, in the above-mentioned experiment no mice died of causes other than spontaneous metastasis of cancer, even when MI-22 was administered every day. Accordingly, Mi-22 is a substance whose safety is very high. Thus it is considered that MI-22 can be used as a cancer metastasis inhibitor (anticancer metastasis agent) with fewer side effects.

[3.3] Cytotoxicity Assay

In order to examine the cytotoxicity (cell growth inhibitory potential) of MI-22, approximately $1\times10^5$ Az521 cells, which were human gastric cancer cells, were plated in each petri dish with a diameter of 3.5 cm and were cultured in the presence or absence (control) of MI-22. Then 6, 12, 24, 36, and 48 hours after the start of culture, the cells in each petri dish were taken off with trypsin-EDTA and then centrifuged. Thereafter the cells were dissolved in 10% FBS-containing DMEM, and then 10 μL of trypan blue was added to 10 μL thereof. After that, the number of cells was counted by the use of a counting chamber. The results are shown in the graphs in FIG. 6. The vertical axis indicates the number of cells, and the horizontal axis indicates the time. The graphs show averages of the results of experiments performed three times.

Figure 6:
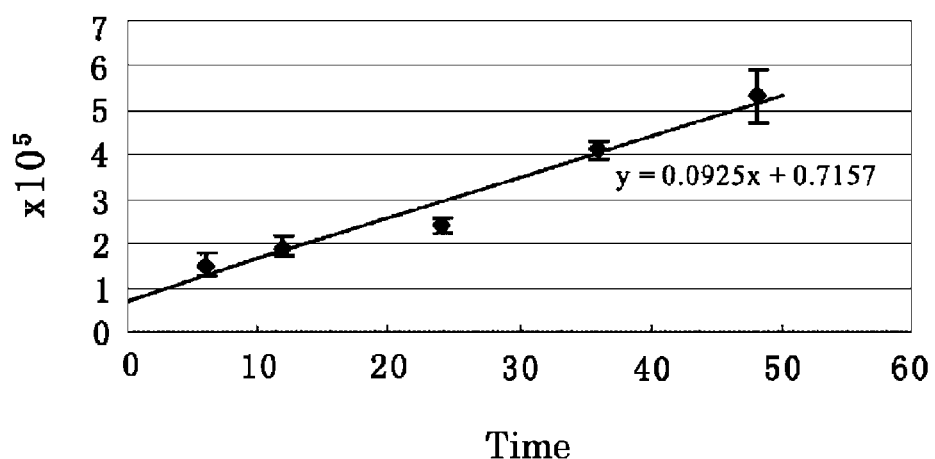
FIG. 6 shows graphs indicating that MI-22 has no cytotoxicity under culture conditions for an Az521 cell, which is a human gastric cancer cell; (a) shows the result of a control in which nothing was added to a culture medium, and (b) shows the result obtained when MI-22 was added to the culture medium.
Figure 6:
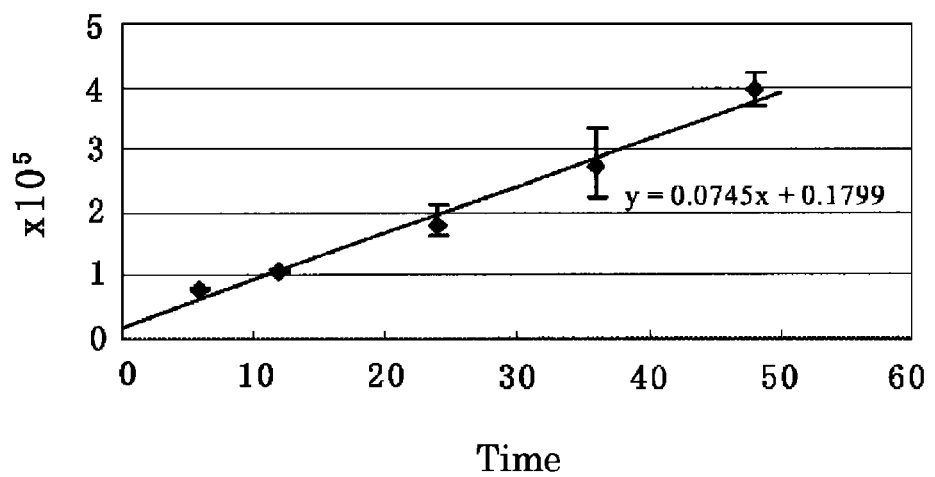

As shown in FIG. 6, there was no significant difference between MI-22 and control. Thus the cytotoxicity (cell growth inhibitory potential) of MI-22 was not found.

Example 4

Inhibition of Cancer Growth by MI-22, Described Above

Az521 cells, which were human gastric cancer cells, were implanted subcutaneously into the back of each nude mouse. Then the cancer growth inhibitory effect (antitumor effect) provided by MI-22 peritoneal administration was examined. More specifically, $1\text{-}2\times10^5$ Az521 cells were injected subcutaneously into the back of each 4-week-old BALB/c nude mouse (nu/nu). Three days before the subcutaneous implantation, 0.1 mL of a solution containing MI-22 (10 mg) dissolved in olive oil (10 mL) was injected intraperitoneally. After the subcutaneous implantation, MI-22 was administered intraperitoneally in the same manner twice a week. For the control mice group, no drug administration/treatment by injection was carried out.

The sizes of tumors formed after the subcutaneous implantation were observed, and then the antitumor effect of MI-22 was evaluated with the weight of the tumors being measured over time. The results are shown in the graph in FIG. 7. The vertical axis indicates the weight (mg) of tumors, and the horizontal axis indicates the number of days after the subcutaneous implantation. The average values of six tumors are shown with respect to three nude mice.

As shown in FIG. 7, in the mice to which MI-22 had been administrated the growth of tumors was suppressed conspicuously as compared to the control mice group. Thus the antitumor effect provided by MI-22 was proved.

Figure 8:
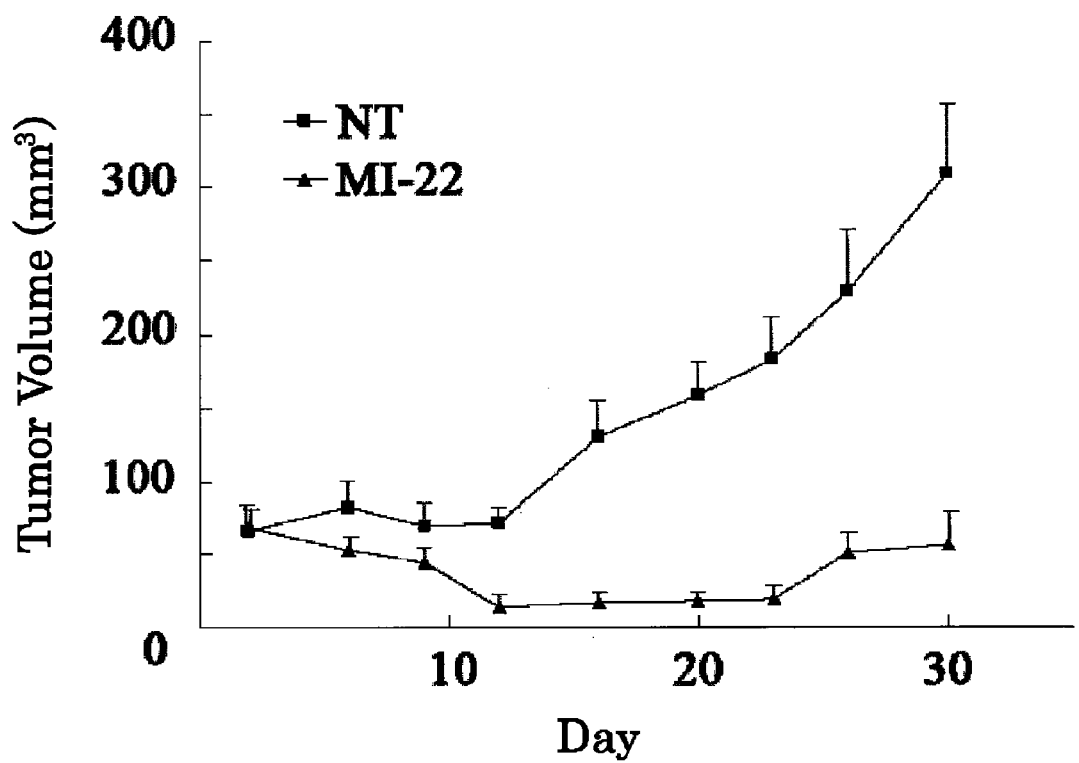
FIG. 8 is a graph indicating the result of study of the antitumor effect of MI-22 administered intraperitoneally to a nude mouse to which a human gastric cancer cell had been implanted subcutaneously.

FIG. 8 shows the results of examination of the antitumor effect of MI-22 that was administered intraperitoneally into nude mice into which Az521 cells, which were human gastric cancer cells, had been implanted subcutaneously in the same experimental method as above. As shown in FIG. 8, in the mice to which MI-22 was administered the increase in the volume of tumors was suppressed conspicuously as compared to the nontreatment mice group (NT). Thus the antitumor effect provided by MI-22 was proved.

These results indicate that MI-22 has outstandingly excellent characteristics that conventional anticancer agents do not have. That is, most of the anticancer agents developed conventionally use the property that "they preferentially inhibit the growth of cancer cells with higher growth potential than that of healthy cells". They also inhibit the growth of healthy cells and therefore have cytotoxicity inevitably. This causes the side effects of anticancer agents, and this disadvantage cannot be avoided. On the contrary, although MI-22 exhibited no cytotoxicity (cell growth inhibitory potential) with respect to healthy cells and cancer cells that were cultured in petri dishes, it did exhibit cell growth inhibitory activity with respect to cancer cells implanted in vivo (in this case, wild mice and nude mice). This characteristic shows that MI-22 is a new type of unprecedented anticancer agent with very high novelty.

INDUSTRIAL APPLICABILITY

As described above, the present invention relates to multimeric oleamide derivatives having connexin 26 inhibitory activities. These novel oleamide derivatives can be used not only as research reagents, but also in a wide industrial field because they exhibit useful bioactivities such as cancer metastasis/growth inhibition. Thus they have various applications, such as in medicines, supplements, and functional foods, in addition to cancer-preventive and cancer-therapeutic drugs.

The invention claimed is:

1. A dimer oleamide derivative represented by the following formula (1) or a pharmacologically acceptable salt thereof:

[Formula 1]

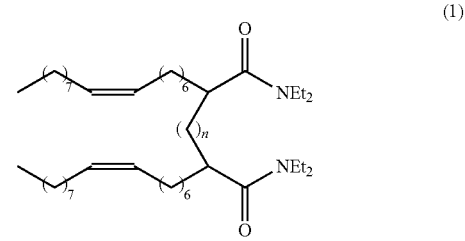

where n denotes an integer of 3, 5, or 8.

2. A food composition comprising the dimeric oleamide derivative of claim 1 or a pharmacologically acceptable salt thereof.

3. A connexin 26 inhibitor comprising the dimeric oleamide derivative of claim 1 or a pharmacologically acceptable salt thereof.

* * * * *

UNITED STATES PATENT AND TRADEMARK OFFICE
CERTIFICATE OF CORRECTION

| | |
|---|---|
| PATENT NO. | : 7,846,972 B2 |
| APPLICATION NO. | : 11/718361 |
| DATED | : December 7, 2010 |
| INVENTOR(S) | : Hiroshi Nojima et al. |

It is certified that error appears in the above-identified patent and that said Letters Patent is hereby corrected as shown below:

Title Page
Face of the patent, INID code (73), the first assignee "The New Industrial Research Organization" should read --The New Industry Research Organization--.

Signed and Sealed this
Ninth Day of August, 2011

David J. Kappos
*Director of the United States Patent and Trademark Office*